(12) United States Patent
Litvin et al.

(10) Patent No.: US 8,000,890 B2
(45) Date of Patent: Aug. 16, 2011

(54) IMAGE-GUIDED NAVIGATION EMPLOYING NAVIGATED POINT COMPUTATION METHOD AND SYSTEM

(75) Inventors: Andrew Litvin, Wakefield, MA (US); Mohamed Ali Hamadeh, Kingston, NH (US)

(73) Assignee: General Electric Company, Niskayuna, NY (US)

( * ) Notice: Subject to any disclaimer, the term of this patent is extended or adjusted under 35 U.S.C. 154(b) by 852 days.

(21) Appl. No.: 11/948,835

(22) Filed: Nov. 30, 2007

(65) Prior Publication Data
US 2009/0143973 A1 Jun. 4, 2009

(51) Int. Cl.
*G01C 21/00* (2006.01)
(52) U.S. Cl. ....................................................... 701/200
(58) Field of Classification Search .................. 701/200; 345/663; 600/407, 409, 420, 424, 427; 348/25, 348/77, 113, 116, 141–143, 169; 382/103, 382/128, 130–132; 378/94, 98, 206, 207
See application file for complete search history.

(56) References Cited

U.S. PATENT DOCUMENTS

| 7,671,887 B2 * | 3/2010 | Pescatore et al. | 348/25 |
| 2006/0094958 A1 * | 5/2006 | Marquart et al. | 600/434 |

OTHER PUBLICATIONS

D. Ritter, M. Mitschke, R. Graumann. Markerless Navigation with the Intra-Operative Imaging Modality SIREMOBILE Iso-$C^{3D}$.

* cited by examiner

*Primary Examiner* — Kim T Nguyen
(74) *Attorney, Agent, or Firm* — Fletcher Yoder (57) ABSTRACT

Provided is a method of image-guided navigation comprising determining a final navigated point in a three-dimensional reconstructed coordinate system based at least partially on two or more navigated points in a coordinate system associated with a two-dimensional array of image pixels and without specifying a coordinate of each of the two or more navigated points in a direction orthogonal to the two-dimensional array of image pixels, wherein each of the two or more navigated points is for a different position of a C-arm gantry. Also provided is an image-guided navigation system.

10 Claims, 5 Drawing Sheets

IMAGE-GUIDED NAVIGATION EMPLOYING NAVIGATED POINT COMPUTATION METHOD AND SYSTEM

BACKGROUND

The present invention relates generally to image-guided navigation. More particularly, the present invention relates to methods and systems that employ a technique for determining a navigated point that uses an image-plane constraint to reduce navigation errors.

Image-guided navigation systems typically include an imaging system and an electromagnetic tracker and have been used to provide an operator (e.g., a physician) with information to assist in the precise and rapid positioning of a medical (e.g., surgical) device in a patient's body. In general, an image may be displayed for the operator that includes a visualization of the patient's anatomy with an icon or image representing the device location projected thereon. As the device is positioned with respect to the patient's body, the displayed image may be updated to reflect the correct device location. The image of the patient's anatomy may be generated either prior to or during the medical or surgical procedure. Moreover, any suitable medical imaging technique, such as X-ray, computed tomography (CT), magnetic resonance imaging (MRI), positron emission tomography (PET), ultrasound, endoscopy, and optical imaging in the UV, visible, and infrared light spectrums may be utilized. For example, navigation may involve taking X-ray projections at different angular positions of a C-arm gantry and subsequent tomographic image reconstruction. With certain techniques, navigation occurs on three-dimensional (3D) images reconstructed from such X-ray projections, shortly before or during the surgical procedure.

To accurately depict the device position and orientation in the coordinate system associated with the reconstructed image, the coordinates associated with the device being employed should be correlated with the reconstructed-image (or "world") coordinate system. This correlation usually involves transforming the device coordinates from the device coordinate system to the world coordinate system via a transform chain that includes a number of intermediate transformations. The last transform in this chain transforms a point from a coordinate system associated with a two-dimensional array of image pixels to the world coordinate system. The coordinate system associated with the two-dimensional array of image pixels may also be referred to as the "image coordinate system."

A particulate feature of 3D navigation systems is the ability to transform the device coordinates from the image coordinate system to the world coordinate system for different gantry positions. In some implementations, the final device coordinates for display on the reconstructed image is computed by averaging the points in the world coordinate system obtained for different gantry positions for which the transform chain is established.

As will be appreciated, image-guided navigation may be complicated by navigation error, which is perceived by the operator as the distance between the tip of the navigated device in the image and the true instrument position in the image. The technique of averaging the points in the world coordinate system for the different gantry positions should reduce the navigation error. However, there is a need for additional techniques to reduce the navigation error on the reconstructed image

BRIEF DESCRIPTION

A method of image-guided navigation, comprising: determining a final navigated point in a three-dimensional reconstructed coordinate system based at least partially on two or more navigated points in a coordinate system associated with a two-dimensional array of image pixels and without specifying a coordinate of each of the two or more navigated points in a direction orthogonal to the two-dimensional array of image pixels, wherein each of the two or more navigated points is for a different position of a C-arm gantry.

A method of image-guided navigation, comprising: manipulating a device inside a patient, wherein an electromagnetic sensor is fixed in relation to the device; transmitting a tracking signal; receiving the tracking signal; determining a position of the device in a three-dimensional reconstructed coordinate system associated with a reconstructed image using the tracking signal, wherein the position of the device is based at least partially on two or more navigated points in the three-dimensional reconstructed coordinate system, wherein each of the two or more navigated points was transformed from a coordinate system associated with a two-dimensional array of image pixels to the three-dimensional reconstructed coordinate system for a different position of a C-arm gantry, and wherein the position of the device is determined using only the X- and Z-coordinates of the two or more navigated points in the coordinate system associated with the two-dimensional array of image pixels; and projecting the position of the device onto the reconstructed image.

An image-guided navigation system, comprising: a device; an electromagnetic sensor fixed in relation to the device; at least one additional electromagnetic sensor fixed in relation to a patient; processing circuitry configured to determine a position of the device in a three-dimensional reconstructed coordinate system based at least partially on two or more navigated points in a coordinate system associated a two-dimensional array of image pixels and without specifying a coordinate of each of the two or more navigated points in a direction orthogonal to the two-dimensional array of image pixels, wherein each of the two or more navigated points is for a different position of a C-arm gantry.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
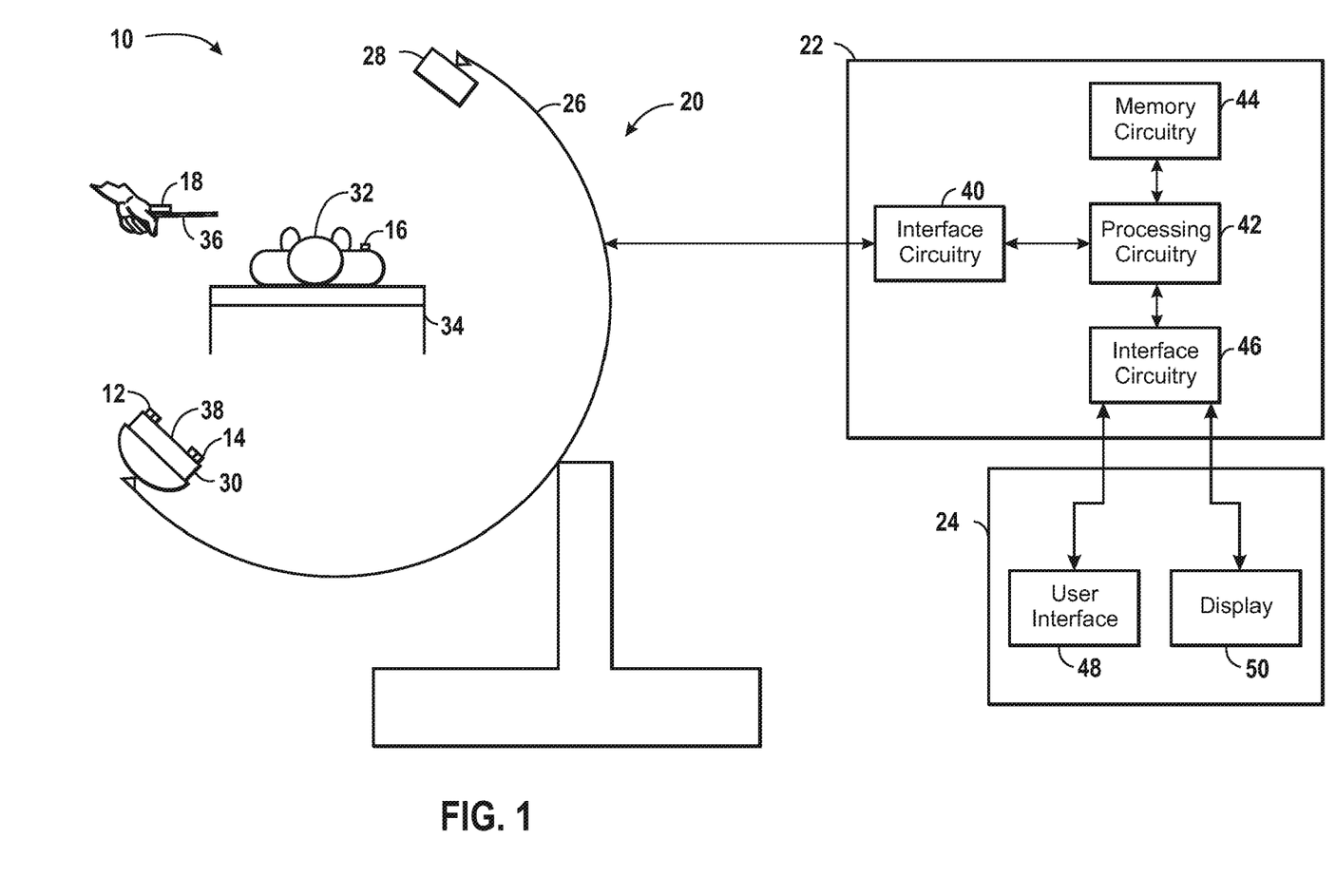
FIG. 1 is an illustration of an example navigation system in accordance with certain aspects of the present technique.

Referring now to FIG. 1, navigation system 10 is illustrated. In the illustrated embodiment, navigation system 10 comprises tracking components that include a plurality of electromagnetic (EM) sensors 12, 14, 16, and 18. Further, navigation system 10 includes an X-ray fluoroscopy system 20 for acquiring and processing image data. As illustrated, navigation system 10 further includes controller 22 and workstation 24.

X-ray fluoroscopy system 20 is illustrated as a C-arm system that includes a C-arm 26, an X-ray radiation source 28, and an X-ray detector 30. The X-ray radiation source 28 is mounted on the C-arm 26, and the X-ray detector 30 is mounted on the C-arm 26 in an opposing location from the X-ray radiation source 28. While in some systems the X-ray radiation source 28 and the X-ray detector 30 may be fixed, in a typical fluoroscopy system the C-arm 26 allows for movement of the X-ray radiation source 28 and the X-ray detector 30 about a patient 32. In operation, the X-ray radiation source 28 emits a stream of radiation suitable for X-ray fluoroscopy. The X-ray detector 30 receives a portion the stream of radiation from the X-ray source 28 that passes through patient 32 positioned on a table 34. The X-ray detector 30 produces electrical signals that represent the intensity of the radiation stream. As those of ordinary skill in the art will appreciate, these signals are suitably acquired and processed to reconstruct an image of features within the subject.

While specific reference is made in the present discussion to an X-ray imaging system, and particularly to a fluoroscopy system, it should be appreciated that the invention is not intended to be limited to these or to any specific type of imaging system or modality. Accordingly, the technique may be used for tracking, in conjunction with other imaging modalities used in real time, or with images acquired prior to a surgical intervention or other procedure.

A plurality of EM sensors may be fixed in relation to the fluoroscopy system. In the illustrated embodiment, first and second sensors 12, 14 are fixed to calibration assembly 38, which is fixed on the X-ray detector 30 of the X-ray fluoroscopy system 20. Third EM sensor 16 may be fixed in relation to the patient 32. As illustrated, third EM sensor 16 is fixed on the patient 32. Fourth EM sensor 18 may be fixed in relation to a medical (e.g., surgical) device 36. In the illustrated embodiment, fourth EM sensor 18 is mounted in the operative end of the medical device 36. Device 36 may be may be any suitable device for use in a medical procedure. For example, device 36 may be a drill, a guide wire, a catheter, an endoscope, a laparoscope, a biopsy needle, an ablation device or other similar devices.

The EM sensors 12-18 may be implemented as EM receivers or EM transmitters, as will be appreciated by those of ordinary skill. In one embodiment, third EM sensor 16 may be implemented as an EM transmitter, while the remaining EM sensors 12, 14, and 18 may be implemented as EM receivers. In this embodiment, the signals sensed by fourth EM sensor 18 that is fixed in relation to the device 36 may be used to determine the location of the device 36, for example, the position and orientation, including the X-, Y- and Z-coordinates and the pitch, yaw, and roll angles. Likewise, the signals sensed by the first and second EM sensors 12, 14 may be used to determine the location of the respective sensor. As will be appreciated, the mutual inductance of two EM sensors is the same, regardless as to which is the receiver and the transmitter. Therefore, relative positioning and functionality of the EM receivers and transmitters may be reversed. For example, the third EM sensor 16 fixed in relation to the patient may be implemented as an EM receiver, while the remaining EM sensors 12, 14, and 18 may be implemented as EM transmitters.

Each of the EM sensors 12-18, for example, may be formed from magnetic dipoles (e.g., coils, current loops, electromagnets, etc.) capable of producing a dipole magnetic field when a current is applied or induced are them. Electromagnetic fields generated by each of the dipoles are distinguishable from one another in phase, frequency, time division multiplexing, and the like. As those of ordinary skill in the art will appreciate, the near-field characteristics of the electromagnetic fields may be used for coordinate determination. In some embodiments, one or more of the EM sensors 12-18 may employ industry-standard coil architecture (ISCA) type coils, a single dipole coil, or a combination thereof. ISCA coils generally may be defined as three, approximately collocated, approximately orthogonal, and approximately dipole coils. Alternatively, one or more of the EM sensors 12-18 may be configured with a single coil that generates a single dipole magnetic field. In addition, one or more of the EM sensors 12-18 may employ technologies other than a coil, including, for example, Hall Effect, magnetoresistance, or flux gate devices. As will be appreciated, the EM sensors 12-18 may operate in a wire or wireless configuration.

As previously mentioned, navigation system 10 further includes controller 22. In the illustrated embodiment, controller 22 includes interface circuitry 40 for receiving tracking and imaging data, processing circuitry 42, memory circuitry 44, and workstation interface circuitry 46 for communicating with workstation 24. As will be appreciated, one or more computers may be used to implement controller 22. In general, processing circuitry 42, which may typically include a digital signal processor, a CPU or the like, may process the tracking data so that the location of the device 36 may be projected onto the reconstructed image. In addition, processing circuitry 42 also may process the imaging data to reconstruct the data into a meaningful diagnostic image. Memory circuitry 44 may serve to save the imaging and tracking data as well as other system parameters.

As illustrated, the navigation system 10 further includes the workstation 24, which includes a user interface 48 and a display 50. The user interface 48 may include a keyboard and/or mouse, as well as other devices such as printers or other peripherals for reproducing hardcopies of the reconstructed images. Display 50 may include one or more screens. For example, the display 50 may include a first screen for displaying a previously acquired image and a second screen for displaying one or more intra-operative images.

Figure 2:
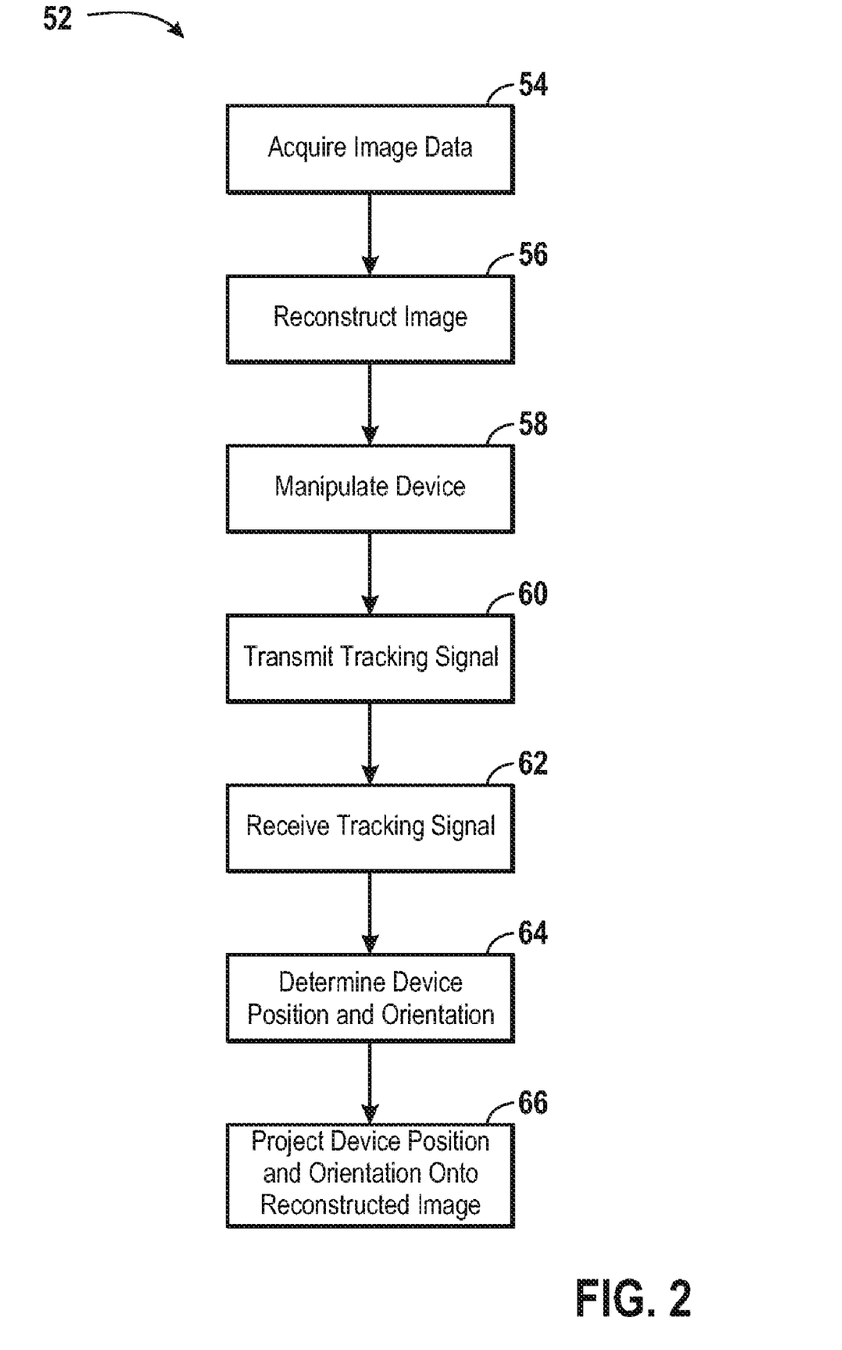
FIG. 2 is a flowchart depicting an example method for surgical navigation in accordance with certain aspects of the present technique.

Referring now to FIG. 2, an example method 52 for using the navigation system 10 to track the device 36 is depicted in flowchart form. As depicted at block 54, the method may include acquiring image data using the X-ray fluoroscopy system 20. For example, a number of different X-ray projections may be taken for different angular positions of the C-arm 26. The method further may include reconstructing an image from the acquired image data, as depicted at block 56. For example, a tomographic image may be reconstructed that includes a 3D image of at least a region of the patient's body.

As depicted at block 58, the method further may include an operator (e.g., a physician) manipulating the device 36. For example, the operator may manipulate the device 36 inside the patient 32. The method further may include transmitting the tracking signal, as depicted at block 60. For example, the third EM sensor 16 may generate a magnetic field. As previously mentioned, the third EM sensor 16 may be fixed in relation to the patient 32. In certain embodiments, the third EM sensor 16 may include a single dipole coil that is provided a drive current to generate a magnetic field having a given magnitude, phase and frequency.

As depicted at block 62, the method further may include receiving the tracking signal. For example, the tracking signal from the third EM sensor 16 may be received by the fourth EM sensor 18. As previously mentioned, the fourth EM sensor 18 is fixed in relation to the device 36. In certain embodiments, the magnetic field generated by the third EM sensor 16 may induce a current across the fourth EM sensor 18, such as across one or more coils in the fourth EM sensor 18.

As depicted at block 64, the method further may include determining the position and orientation of the device 36. For example, the tracking signal received by the fourth EM sensor 18 may be used to determine the position and orientation of the fourth EM sensor 18. The tracked position and orientation of the fourth EM sensor 18 may then be used to determine the position and orientation of the device 36, such as the tip of the device 36. For instance, the relative positions of the fourth EM sensor 18 and the device 36 may be known such that the position and orientation of the fourth EM sensor 18 may be correlated to the position and orientation of the device 36. Even further, the relative positions of the fourth EM sensor 18 and the tip of the device 36 may be known such that the position and orientation of the fourth EM sensor 18 may be correlated to the position and orientation of the tip of the device 36. As will be appreciated, distortion may be accounted for in this determination.

The position and orientation of the device 36 may be determined in the coordinate system associated with the device 36. This position in the device coordinate system may then be correlated to the coordinate system associated with the reconstructed image (or the "world coordinate system"). This correlation usually involves transforming the device coordinates from the device coordinate system to the world coordinate system via a transform chain that includes a number of intermediate transformations. The last transform in this chain transforms a point from a coordinate system associated with a two-dimensional array of image pixels to the world coordinate system. The coordinate system associated with the two-dimensional array of image pixels may also be referred to as the "image coordinate system." The 3D extrinsic transform equation for this final transformation is given by the following equation:

$$X_i^{IMAGE} = A_i X^{WORLD} + T_i \quad (1)$$

wherein $X_i^{IMAGE}$ is the coordinates for the navigated point in the image coordinate system of the $i^{th}$ gantry position; $X^{WORLD}$ is the coordinates for the navigated point in the world coordinate system; and $(A_i, T_i)$ defines the 3D extrinsic transform for $i^{th}$ gantry position.

As depicted at block 66, the method further includes projecting the position and orientation of the device 36 onto the reconstructed image. By way of example, an icon or image representing the device 36 (or the device tip) position and orientation may be projected onto the reconstructed image. The operator of the device 36 should be able to use this visualization of the device 36 on the reconstructed image to assist in the manipulation of the device 36 within the patient 32. For example, the visualization of the device 36 may assist the operator in the precise and rapid positioning of the device 36 within the patient 32. As will be discussed in more detail below, embodiments of the present technique should reduce navigation errors, allowing more precision in the tracking of the device 36.

Figure 3:
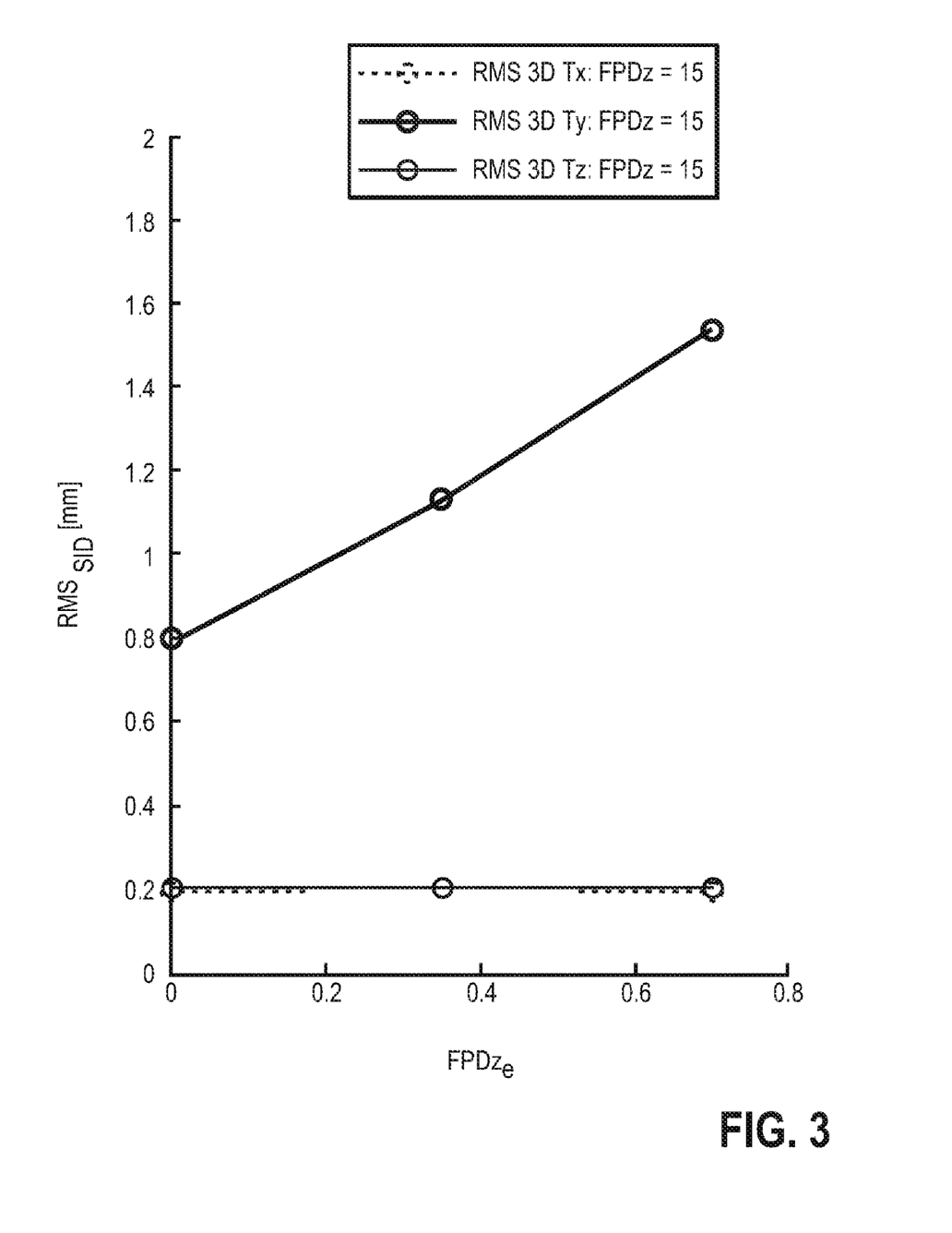
FIG. 3 is a graphical illustration of modeled navigation errors of the image-to-world coordinate system transform, in accordance with certain aspects of the present technique.

As will be appreciated, image-guided navigation may be complicated by navigation error, which is perceived by the operator as the distance between the tip of the navigated device in the image and the true instrument position in the image. It has been determined through modeling and numerical simulations that navigation errors in 3D navigation may be strongly dependent on the uncertainty (e.g., error) in the knowledge of the vertical shift between the coordinate system of the flat panel detector grid and the image coordinate system (referred to herein as the "FPDz"). This vertical shift is typically dictated by the mechanical design and generally cannot be directly measured with high accuracy. For example, an uncertainty in FPDz of ±0.7 mm may be specified for a particular configuration. Numerical simulations suggest that the error in FPDz propagates into error in the source-to-image distance (SID) in the course of intrinsic parameters calibration, which is in turn reflected in a relatively high error in translation in the y-axis (Ty) 3D extrinsic parameter, which controls the along-projection-line displacement of the world coordinate with respect to the image coordinate system. FIG. 3 is a graphical illustration of modeled root mean square (RMS) errors as a function of uncertainty FPDz for the image-to-world transform. More particularly, the RMS errors for three translation components (Tx, Ty, and Tz) are illustrated as a function of FPDz for the image-to-world Transform. For this illustration, the FPDz is 15 mm. As illustrated in FIG. 3, the Ty parameter, corresponding to the direction orthogonal to the XZ plane in the image coordinate system, has the highest error. Indeed, the Ty parameter has an error 4-6 times larger than in the XZ plane of the image coordinate system (given by the errors in the 3D extrinsic Tx, Tz parameters). The errors in the 3D extrinsic transform rotation matrix A are assumed to be small for the modeled RMS errors shown in FIG. 3.

As previously mentioned, a particular feature of 3D navigation systems is the ability to transform the navigated point (e.g., the device-tip coordinates) from the image coordinate system to the world coordinate system for different gantry positions. Accordingly, a navigated point with associated coordinates in the world coordinate system may be obtained for each gantry position. To obtain the final coordinates for display on the reconstructed image, the navigated points for each gantry position may be averaged. This methodology should be beneficial in reducing navigation error (i.e., the distance between the tip of the navigated device in the image and the true device position) where the errors for different gantry positions are independent. However, as discussed above, the errors due to the uncertainty in the FPDz are the same for different gantry positions, leading to the bias component of error in SID and Ty for different gantry positions, possibly leading to high navigation errors.

Figure 4:
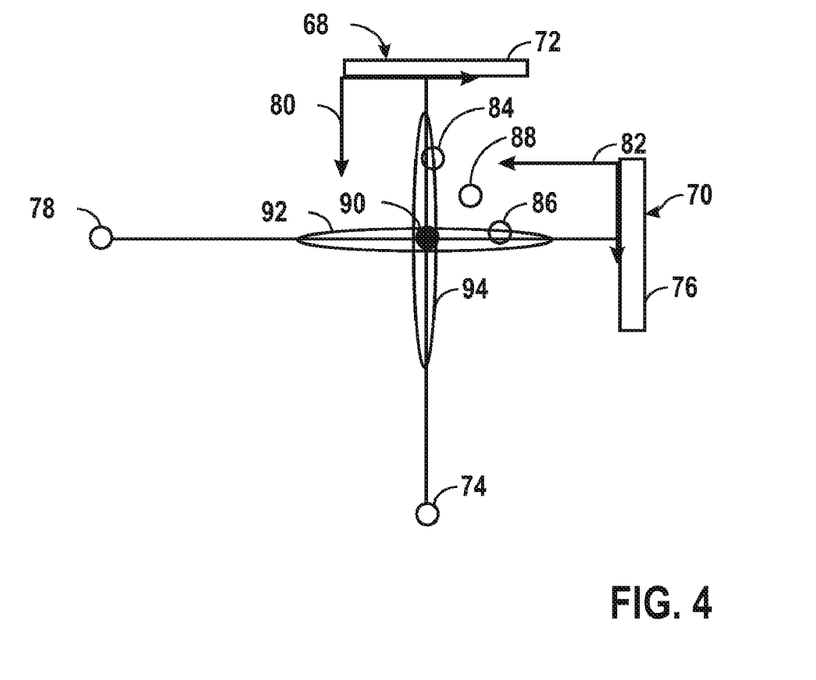
FIG. 4 is an illustration of the error in determining a navigated point using an averaging technique.

FIG. 4 illustrates the error in the navigated point for the averaging technique discussed above. In the illustrated embodiment, a navigated point is determined for two different gantry positions. The first gantry position is generally referred to by reference number 68, and the second gantry position is generally referred to by reference number 70. For the first gantry position 68, the flat panel detector 72 and the X-ray source 74 are illustrated. For the second gantry position 70, the flat panel detector 76 and the X-ray source 78 are illustrated. Further, the y-axes for the image coordinate system for the first gantry position 68 and the second gantry position 70 are generally referred to by reference numbers 80 and 82, respectively. A first navigated point 84 is also illustrated that has been transformed into the world coordinate system from the image coordinate system for the first gantry position 68. A second navigated point 86 is also illustrated that has been transformed into the world coordinate system from the image coordinate system for the second gantry position 70. As described above, the final navigated point for projection onto the reconstructed image may be determined by averaging the first navigated point 84 and the second navigated point 86. Accordingly, the final averaged navigated point in the world coordinate system is illustrated by the reference number 88.

Reference numeral 90 illustrates the true navigated point (e.g., the true coordinates of the tip of the device) in the world coordinate system. FIG. 4 also illustrates the confidence intervals for the navigated point transformed into the world coordinate system for two gantry positions. As illustrated, the x-axis confidence interval 92 and the y-axis confidence interval 94 are shown with respect to the true navigated point 90. As previously mentioned, averaging the navigated points for different gantry position may result in high navigation errors due to, for example, uncertainty in the FPDz. As illustrated by FIG. 4, the final navigated point 88 is located outside the intersection of confidence intervals 92 and 94 that are obtained using gantry positions 68 and 70 respectively, indicating undesirable error in the final navigated point 88.

As will be appreciated, each gantry position (such as the first gantry position 68 and the second gantry position 70) yields a transform that constrains the navigated point in the x-direction, the y-direction, and the z-direction for the image coordinate system. However, because of uncertainty in the FPDz, the navigated point may not be well defined in the y-direction. The other two directions, the x- and z-directions, should generally have low error. In accordance with aspects of the present technique, the navigated point for each of the gantry positions in the world coordinate system may be averaged with a constraint imposed on the navigated point in the image coordinate system for each used gantry position. As will be appreciated, this constraint approach used only the precise components of the transform. In other words, for each gantry position, only the x- and z-components of the navigated point are used to determine the final navigated point. In this manner, the coordinates of the navigated point in the XZ plane of the image coordinate system are specified, while the coordinate of the navigated point in the direction orthogonal (the y-direction) to the XZ plane of the image coordinate system is not used.

Figure 5:
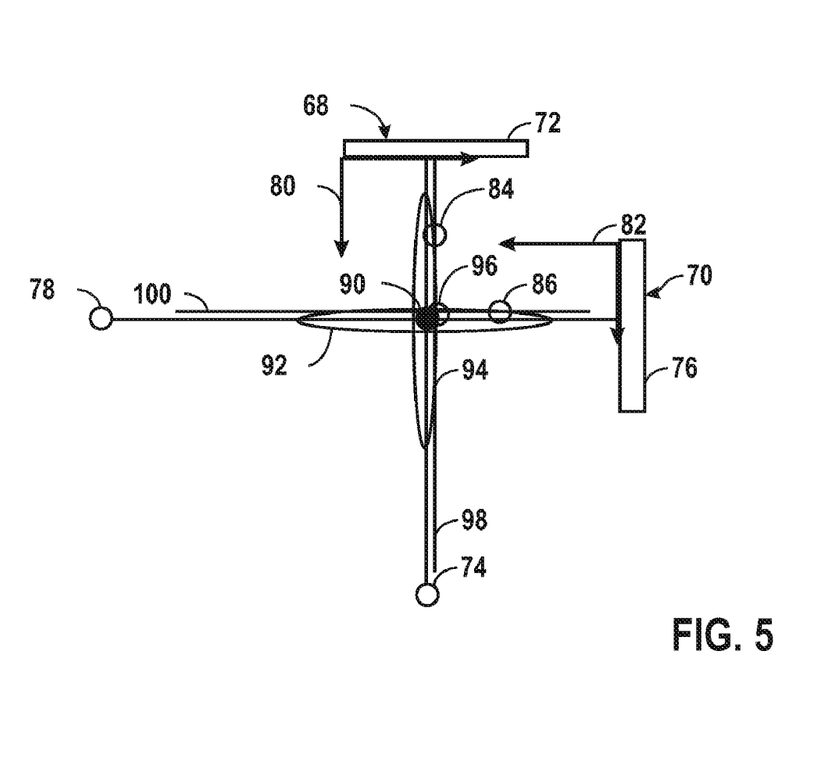
FIG. 5 is an illustration of a process for determining a navigated point, in accordance with certain aspects of the present technique.

FIG. 5 illustrates a technique for determining the final navigated point using only the x- and z-components of the transform, in accordance with embodiments of the present technique. In the illustrated embodiment, a navigated point is determined for two different gantry positions. The first gantry position is generally referred to by reference number 68, and the second gantry position is generally referred to by reference number 70. For the first gantry position 68, the flat panel detector 72 and the X-ray source 74 are illustrated. For the second gantry position 70, the flat panel detector 76 and the X-ray source 78 are illustrated. Further, the y-axes for the image coordinate system for the first gantry position 68 and the second gantry position 70 are generally referred to by reference numbers 80 and 82, respectively. A first navigated point 84 is also illustrated that has been transformed into the world coordinate system from the image coordinate system for the first gantry position 68. A second navigated point 86 is also illustrated that has been transformed into the world coordinate system from the image coordinate system for the second gantry position 70.

In accordance with the present technique, the final navigated point 96 may be determined by averaging the first navigated point 84 and the second navigated point 86 using only their respective x- and z-components. It should be noted that the first navigated point 84 and the second navigated point 86 are shown in FIG. 5 at their respective x-, y-, and z-coordinates in the world coordinate system. However, as mentioned above, the final navigated point 96 may be determined without the y-component for each gantry position, but rather using only the x- and z-components. Accordingly, the coordinate of the navigated point in the direction orthogonal to the XZ plane of the image coordinate system (or the y-direction) is relaxed. As illustrated by FIG. 5, this relaxation implies that the final navigated point 96 is positioned on a line in a direction orthogonal to the XZ plane that passes through the x- and z-coordinates for the first navigated point 84 and the second navigated point 86, respectively. The first line 98 orthogonal to the XZ plane of the image coordinate system for the first gantry position 68 and the second line 100 orthogonal to the XZ plane for the second gantry position 70 are both illustrated on FIG. 5. The first line 98 and the second line 100 may be triangulated to determine the position of the final navigated point 96 in the world coordinate system. For example, the final navigated point 96 is located at the intersection of the first line 98 and the second line 100, in the illustrated embodiment.

The true navigated point (e.g., the true coordinates of the tip of the device) in the world coordinate system is illustrated by reference number 90. FIG. 5 also illustrates the confidence intervals for the navigated point transformed into the world coordinate system for two gantry positions. As illustrated, the x-axis confidence interval 92 and the y-axis confidence interval 94 are shown with respect to the true navigated point 90. As illustrated by FIG. 5, the final navigated point 96 is located inside both the x-axis confidence interval 92 and the y-axis confidence interval 94.

As will be appreciated, embodiments of the present technique may be extended to more than two gantry positions. In such embodiments, the final navigated point may be computed as the best point satisfying the constraints in the Least Squares sense. Accordingly, the final navigated point may be found as the coordinates minimizing the sum (over utilized gantry positions) of squared differences in the XZ plane of the image coordinate system between the navigated point rotated by the matrix $A_i$ and the point ($x_i^o$, $y_i^o$, $z_i^o$). More particularly, the final navigated point ($\tilde{x}$, $\tilde{y}$, $\tilde{z}$) in the world coordinate system may be determined using the following equation:

$$(\tilde{x}, \tilde{y}, \tilde{z}) = \underset{x,y,z}{\operatorname{argmin}} \sum_{i=1}^{M} \left( \left[ A_i \begin{pmatrix} x \\ y \\ z \end{pmatrix} \right]_x - x_i^o \right)^2 + \left( \left[ A_i \begin{pmatrix} x \\ y \\ z \end{pmatrix} \right]_z - z_i^o \right)^2 \quad (2)$$

wherein M is the number of gantry positions; $x_i^o$ is the x-coordinate of the navigated point in the image coordinate system for the $i^{th}$ gantry position; $y_i^o$ is the y-coordinate of the navigated point in the image coordinate system for the $i^{th}$ gantry position; where matrices $A_i$ represent the transform between the real world coordinate system and the image coordinate system for the $i^{th}$ gantry position. As will be appreciated, the objective function to be minimized is quadratic and the unique solution may be found by solving the system of linear equations. By way of example, the objective function may be solved with analytic solution or numeric gradient decent using the MATLAB optimization toolbox. While equation (2) shown above is quadratic, it should be appreciated that a non-quadratic objective function (e.g., half-quadratic) may be employed. A non-quadratic objective function, for example, may make the technique more robust to outlier errors. In addition, individual terms for different gantry positions may be weighted differently where additional information on the calibration accordance of the gantry positions is provided. Such information may be provided, for example, by calibration residual reprojection error metrics and the like.

Figure 6:
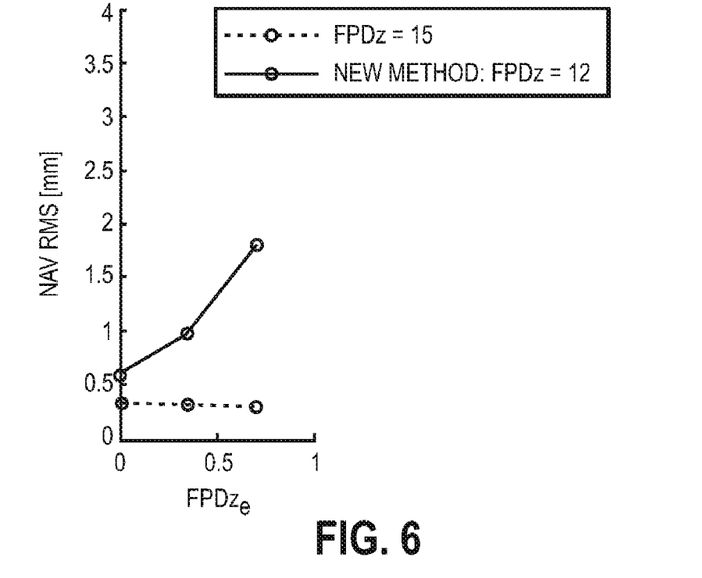
FIGS. 6-7 are graphical illustrations of modeled navigation errors of the image-to-world coordinate system transform, in accordance with certain aspects of the present technique.

FIG. 6 is a graphical illustration of modeled navigation errors of the image-to-world coordinate system transform. More particularly, FIG. 6 illustrates a comparison of navigation accuracy for the above-discussed averaging technique with the constraint approach of embodiments of the present technique. For this comparison, only two gantry positions were used that were approximately orthogonal. For each technique, the RMS error is illustrated as a function of the standard deviation of the FPDz for the Ty parameter of the image-to-world transform. For this illustration, the FPDz was approximately 15 mm. As illustrated by FIG. 6, the RMS error increases with increasing uncertainty in FPDz for the averaging technique, indicating that navigation accuracy is dependent on uncertainty of FPDz. However, the RMS error for the constraint technique of embodiments of the present technique is independent of uncertainty in FPDz, indicating that the navigation accuracy of the constraint technique of embodiments of the present technique is independent of uncertainty of FPDz.

Figure 7:
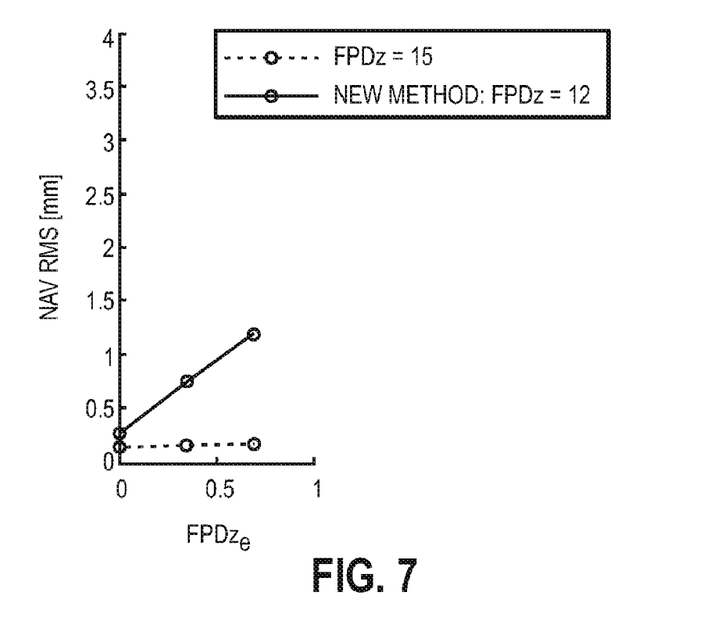

FIG. 7 is another graphical illustration of modeled navigation errors of the image-to-world coordinate system transform. More particularly, FIG. 7 illustrates a comparison of navigation accuracy for the above-discussed averaging technique with the constraint approach of embodiments of the present technique. For these comparison, 160 gantry positions were used to produce the point in the world coordinate system. For each technique, the RMS error is illustrated as a function of the standard deviation of the FPDz for the Ty parameter of the image-to-world transform. For this illustration, the FPDz was approximately 15 mm. Similar to FIG. 6, the RMS error for the constraint technique of embodiments of the present technique is independent on uncertainty in FPDz, indicating that the navigation accuracy of the constraint technique of embodiments of the present technique is independent of uncertainty of FPDz, as illustrated by FIG. 7.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of image-guided navigation, comprising: determining, via processing circuitry that receives signals generated by a sensor, a final navigated point in a three-dimensional reconstructed coordinate system based at least partially on two or more navigated points in a coordinate system associated with a two-dimensional array of image pixels and without specifying a coordinate of each of the two or more navigated points in a direction orthogonal to the two-dimensional array of image pixels, wherein each of the two or more navigated points is for a different position of a C-arm gantry.

2. The method of claim 1, wherein the coordinates of each of the two or more navigated points in the XZ plane of the coordinate system associated with the two-dimensional array of image pixels are specified in the determination of the final navigated point.

3. The method of claim 1, wherein determining the final navigated point comprises utilizing the following equation:

$$(\tilde{x}, \tilde{y}, \tilde{z}) = \operatorname*{argmin}_{x,y,z} \sum_{i=1}^{M} \left( \left[ A_i \begin{pmatrix} x \\ y \\ z \end{pmatrix} \right]_x - x_i^o \right)^2 + \left( \left[ A_i \begin{pmatrix} x \\ y \\ z \end{pmatrix} \right]_z - z_i^o \right)^2$$

wherein M is a number of gantry positions; $x_i^o$ is the x-coordinate of one of the two or more navigated points in the coordinate system associated with the two-dimensional array of image pixels for $i^{th}$ gantry position; $y_i^o$ is the y-coordinate of one of the two or more navigated points in the coordinate system associated with the two-dimensional array of image pixels for $i^{th}$ gantry position; and matrices $A_i$ represent the transform between the real world coordinate system and the image coordinate system for the $i^{th}$ gantry position.

4. The method of claim 1, wherein determining the final navigated point comprises utilizing a quadratic objective function.

5. The method of claim 1, wherein determining the final navigated point comprises utilizing a half-quadratic objective function.

6. The method of claim 1, wherein two or more positions of the C-arm gantry are weighted differently in determining the final navigated point.

7. An image-guided navigation system, comprising:
a device;
an electromagnetic sensor fixed in relation to the device;
at least one electromagnetic sensor fixed in relation to a patient; and
processing circuitry configured to determine a position of the device in a three-dimensional reconstructed coordinate system based at least partially on two or more navigated points in a coordinate system associated a two-dimensional array of image pixels and without specifying a coordinate of each of the two or more navigated points in a direction orthogonal to the two-dimensional array of image pixels, wherein each of the two or more navigated points is for a different position of a C-arm gantry.

8. The image-guided navigation system of claim 7, wherein the electromagnetic sensor fixed in relation to the device is configured to emit a signal.

9. The image-guided navigation system of claim 7, wherein the at least one electromagnetic sensor fixed in relation to the patient is configured to receive a signal.

10. The image-guided navigation system of claim 7, wherein the processing circuitry is configured to specify coordinates of each of the two or more navigated points in the XZ plane of the coordinate system associated with the two-dimensional array in the determination of the position of the device.

* * * * *